(12) United States Patent
Kovacevic

(10) Patent No.: US 6,262,097 B1
(45) Date of Patent: Jul. 17, 2001

(54) SYNERGISTIC WOOD PRESERVATIVE COMPOSITIONS

(76) Inventor: Snezana Kovacevic, 17-460 W. 16th Avenue, Vancouver B.C. (CA), V5Y 1Z3

( * ) Notice: Subject to any disclaimer, the term of this patent is extended or adjusted under 35 U.S.C. 154(b) by 0 days.

(21) Appl. No.: 09/443,868

(22) Filed: Nov. 19, 1999

Related U.S. Application Data

(60) Provisional application No. 60/108,988, filed on Nov. 18, 1998.

(51) Int. Cl.[7] ................................................ A61K 31/425
(52) U.S. Cl. ........................ 514/372; 514/642; 514/643; 422/26; 422/27; 422/28; 422/32; 422/37; 422/40
(58) Field of Search ..................................... 514/372, 642, 514/643; 422/26, 27, 28, 32, 37, 40

(56) References Cited

U.S. PATENT DOCUMENTS 4,906,651 * 3/1990 Hsu ........................................ 514/372
4,950,685 * 8/1990 Ward ..................................... 514/479

* cited by examiner

*Primary Examiner*—Frederick Krass
(74) *Attorney, Agent, or Firm*—Oyen Wiggs Green & Mutala

(57) ABSTRACT

This invention relates to the synergistic wood preservative composition comprising of a quaternary ammonium compound and N-substituted isothiasolones having the properties of providing effective and broader control of microorganisms that produce stain, can cause the deterioration of wood, or may develop resistance to some of the active components.

13 Claims, 2 Drawing Sheets

SYNERGISTIC WOOD PRESERVATIVE COMPOSITIONS

This application claims the benefit of U.S. Provisional Application No. 60/108,988 filed Nov. 18, 1998.

REFERENCE CITED

U.S. Patent Documents
4,906,651 . . . March/1990 . . . Hsu . . . 514/479
5,131,939 . . . July/1992 . . . Hsu . . . 424/405

Other Publications
1. Byrne Tony, *Lumber Protection in the 90's*, Proceedings of meeting held at: FORINTEK CANADA CORP., Western laboratory, 1992.
2. Henderson, N. D., *A review of the Environmental Impact and Toxic Effects of DDAC*, BC Environment Ministry of Environment Land and Parks, Victoria, 1992.
3. Konasewich et al., *Antisapstain Wood Protection*, Environment Canada, BC Environment, 1994.
4. Moore-Landecker, E., *Fundamentals of the Fungi*, Pretice Hall, Englewood Cliffs, N.J., 1990.
5. Webster John, *Introduction to Fungi*, Alden & Mowbray LTD, Oxford, 1970.

BACKGROUND OF THE INVENTION

Timbers with a risk of wetting are often exposed to infestation with moulds, blue staining fungi, or wood destroying fungi. To prevent their surface growth, the wood is traditionally treated with chemical pesticides, commonly called "antisapstain products". The efficacy of these products depends upon their direct toxicity and their ability to create an unfriendly environment that can discourage fungal growth.

In the past, a large volume of chlorophenol compounds were used in order to protect wood from attacks by various pests. Concerns about acute toxicity, occupational impacts, and the presence of hazardous impurities, including dioxins and furans, in chlorophenols are among the reasons for the dissatisfaction with their use. In recent years, there has been a demand for wood preservatives that do not contain chemicals suspected of environmental and human safety problems. However, no system developed so far is believed to be ideal (Byrne, 1992).

The information based on the number of research papers (Byrne, 1992; Konasewich et al., 1994) suggest that didecyldimethyl ammonium chloride was the most effective of the alkilammonium compounds against several wood-destroying fungi, and has been also used against mould and sapstain during storage and transit (anti-sapstain control). Investigating N-substituted isothiasolones for the control of wood destroying fungi shows that they effectively control a wide variety of microorganisms at low levels of active ingredient.

This invention is directed to synergistic compositions of didecyldimethyl ammonium chloride and isothiazolones that are capable of broadening the spectrum of biocidal activities by overcoming the disadvantages caused by actions of micro organisms which may degrade alkilammonium compounds.

BRIEF DESCRIPTION OF THE INVENTION

This invention relates to antisapstain compositions comprising of a synergistic combination of a quaternary ammonium compound, more particularly to didecyldimethyl ammonium chloride (DDAC) which has the structural formula:

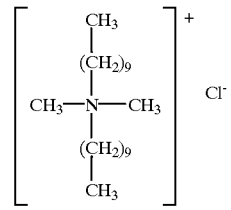

and 3:1 mixture of two isothiazolones (ITA) identified by the IUPAC system of nomenclature as:

5-chloro-2-methyl-4-isothiazolin-3-one
2-methyl-4-isothiazolin-3-one

The corresponding structural formulas are:

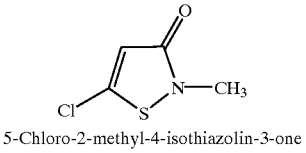

5-Chloro-2-methyl-4-isothiazolin-3-one

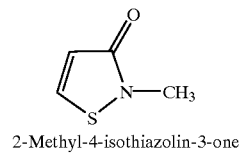

2-Methyl-4-isothiazolin-3-one

A DETAILED DESCRIPTION OF THE INVENTION

Figure 1:
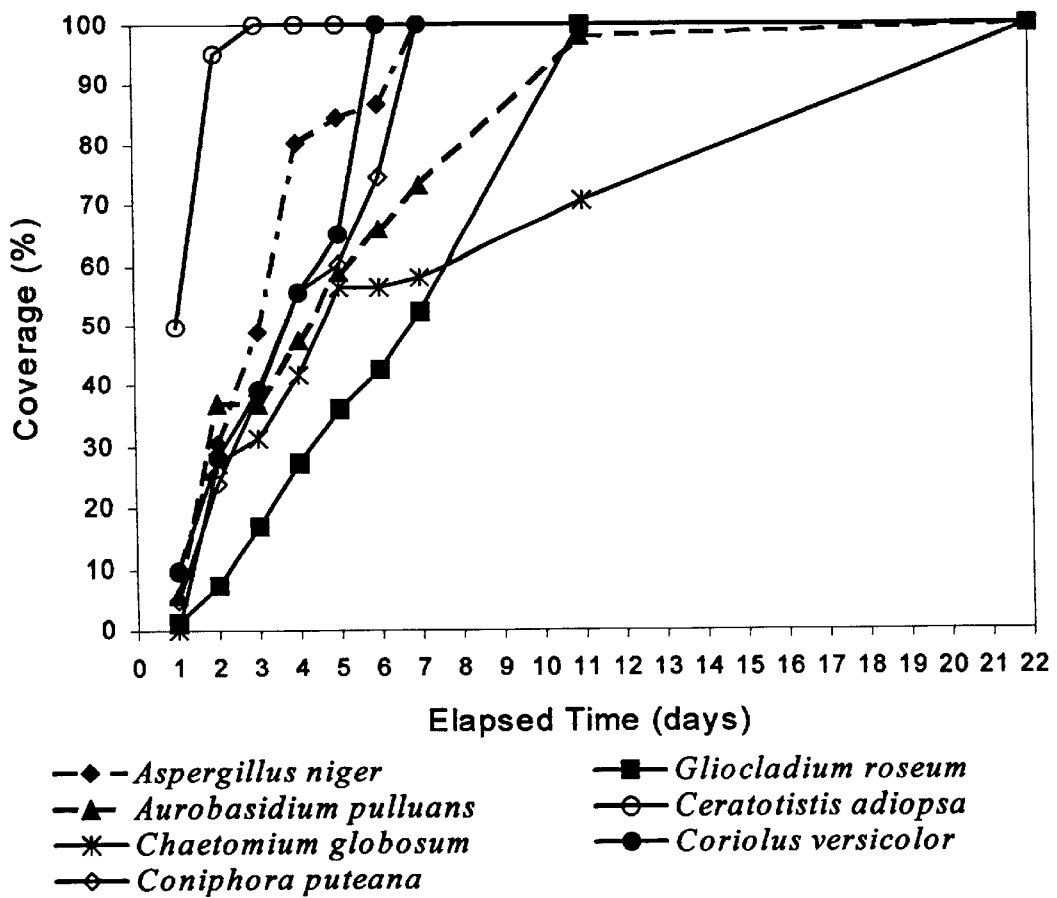
FIG. 1 is a graph depicting the viability of various fungal species on untreated growth media. Growth is measured as a percentage of the media surface covered by a single colony of fungus. *Aspergillus niger* (♦), *Ceratocistis adiposa* (×), *Coniphora puteana* (+), *Coriolus versicolor* (●), *Gliocladium roseum* (■), *Aureobasidium pullulans* (▲), *Chaetomium globosum* (*).
Figure 2:
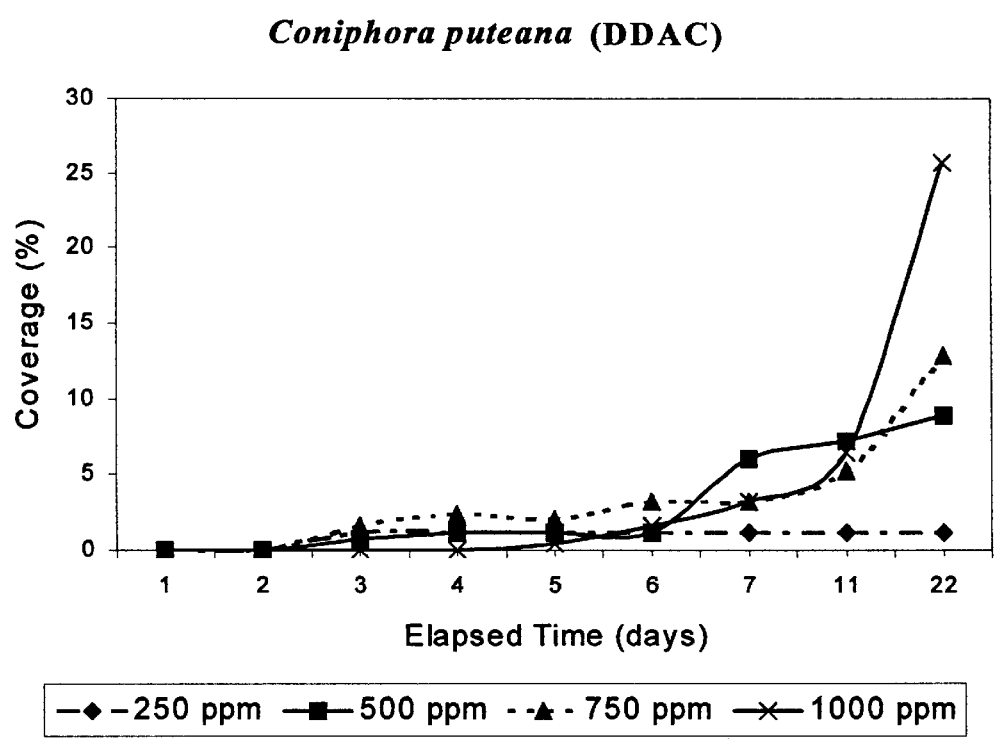
FIG. 2 is a graph depicting the growth rate of *Coniphora puteana* on media containing varying concentrations of DDAC. Growth is measured as a percentage of the media surface covered by a single colony of fungus. Growth at 250 ppm DDAC (♦), 500 ppm (■), 750 ppm (▲), and 1000 ppm (×).

The antisapstain compositions of the invention can be prepared as solutions or emulsions by conventional means using water as a solvent. A preferred form is to combine a water solution of DDAC, and a water solution of ITA.

In the preparation of the composition of the invention, process conditions must be carefully controlled. The pH of the ITA is adjusted to the alkaline range, preferably to a pH of 7 to 11, most preferably from 9 to 10. This may be accomplished by the addition of alkaline material such as sodium or ammonium hydroxide, sodium carbonate, sodium acetate or alike. Thereafter, the diluted ITA should be mixed for a period of 20 min. to 40 min. at ambient temperature. The addition of a diluted quaternary ammonium compound to the solution of ITA also must be done slowly and subsequently for a total of at least 1 hour.

The quantity and ratio of DDAC and ITA will depend upon the specific application. Generally, the preservative composition will contain from about 1 to 300 parts by weight DDAC per about 1 to 5 parts by weight of ITA. The concentrate is generally diluted to working solution strength by the addition of water (or an other solvent). Depending on the severity of the environmental conditions, the concentrate may be diluted about 10 to 200 times with water. Buffers, anticorrosive, as well as iron chelating compounds may also be added.

The resulting solution can be applied to wood by conventional treating methods such as immersion, brush, spray or pressure.

The following example will serve to illustrate the invention and preferred embodiments thereof. All parts and percentages in said examples and elsewhere in the specification and claims are by weight unless otherwise indicated.

EXAMPLE 1

To show the efficacy of a candidate preservative on wood deteriorating microorganisms, a range of concentrations of DDAC and ITA (table 4, 5 and 6) were submitted through microbiological screening test.

DDAC was obtained from Lonza Inc. of Fair Lawn, N.J. as a water solution under the trade name Bardac 2280. The mixture of isothiazolones (ITA) was obtained from Rohm and Haas Canada, under the trade name Kathon 886 F.

To confirm the synergistic effect, these two active components were mixed in different ratios and diluted in water to provide the concentration of active ingredients shown at Table 7. Obtained solutions were later submitted through the microbiological screening test to demonstrate their toxicological characteristics.

For example, to prepare a composition that contains 250 ppm of DDAC and 15 ppm of ITA, the ratio of components used is presented at Table 1:

TABLE 1

| INGREDIENT | % BY WEIGHT |
| --- | --- |
| Bardac 2280 | 0.03 |
| Kathon 886 F | 0.01 |
| Water | 99.96 |

The composition of Bardac 2280 as obtained from its manufacturer is as follows:

TABLE 2

| Bardac 2280 | |
| --- | --- |
| COMPONENT | % BY WEIGHT |
| Didecyldimethyl ammonium chloride | 80.00 |
| Ethanol | 10.00 |
| Water | 10.00 |

The composition of Kathon 886 F as obtained from its manufacturer is as follows:

TABLE 3

| Kathon 886F | |
| --- | --- |
| COMPONENT | % BY WEIGHT |
| Active Ingredients | |
| 5-chloro-2-methyl-4-isothiazolin-3-one: | 8.6% min. |
| 2-methyl-4-isothiazolin-3-one: | 3.6% min. |
| Minimum Value | 11.2% min. |
| Typical Value | 14.2% min. |
| Inert Ingredients: | 25.3% min. |
| Water: | 63.5% min. |

In this bioassay all microorganisms that represent different kinds of fungi are obtained from Forintek Canada Corp:

moulds: *Aspergillus niger* and *Gliocladium roseum* staining fungi: *Aureobasidium pullulans* and *Ceratocistis adiposa* soft rot fungi: *Chaetomium globosum* brown rot fungi: *Coniphora puteana* white rot fungi: *Coriolus versicolor*

In order to examine the toxic effectiveness of DDAC and ITA, solutions of 4% malt agar was prepared and sterilized at 121° C. for 20 minutes (at 103 KPa). Once the malt agar cooled to "hand hot", the previously prepared DDAC and ITA solutions were added in to obtain the range of different concentrations as it is shown in Table 4 and Table 5. For example: in order to produce a concentration of 500 ppm DDAC in the media, 7.5 ml of the 0.4% stock solution of DDAC was added to 112.5 ml of 4% agar. 10 ml of each solution, was transferred into petry plates and allowed to solidify. Specific fungi from culture plates were placed in the center of each plate.

Fungal growth was evaluated by monitoring the diameter of a developing colony on agar over a period of time. Three replicas of every fungicide were prepared and measured. The measurements were converted to express the percentage of the plate's surface. The above procedure was repeated for the toxicological evaluation of each concentration of component or composition presented in Table 4, 5, 6, and 7 for every microorganism that was tested. (Moore-Landecker, E., 1990).

To evaluate the viability of each inoculum, control plates were examined in each test for each microorganism. As seen in FIG. 1, they showed a normal growth.

The results from FIG. 1 indicate that inoculum used was viable and the lack of growth in the treated plates can only be attributed to the presence of DDAC, ITA or their mixture in the media. The effectiveness on all seven examined microorganisms, for each component (DDAC and ITA), is presented in Table 4 and Table 5.

TABLE 4

The growth of *Aspergillus niger* (1), *Gliocladium roseum* (2), *Aureobasidium pullulans* (3), *Ceratocistis adiposa* (4), *Chatemonium globssum* (5), *Trametis coriolus* Versicolor (6), and *Coniphora puteana* (7) in the agar media containing selected concentrations of DDAC.

| Concentration (ppm) | Fungi ( ) | Incubation Period (days) | | | | | | | | |
|---|---|---|---|---|---|---|---|---|---|---|
| | | 1 | 2 | 3 | 4 | 5 | 6 | 7 | 11 | 22 |
| | | | | | Growth Rate (%) | | | | | |
| 250 | 1 | 0.24 | 1.2 | 2.41 | 3.61 | 6.02 | 9.64 | 11.2 | 20.9 | 45.8 |
| 500 | 1 | 0.24 | 0.48 | 1.2 | 2.17 | 3.21 | 5.22 | 7.23 | 16.9 | 35.7 |
| 750 | 1 | 0.24 | 0.48 | 0.64 | 0.88 | 1.2 | 2.41 | 3.61 | 9.24 | 23.7 |
| 1000 | 1 | 0.24 | 0.32 | 0.32 | 0.4 | 0.72 | 1.2 | 2.41 | 28.1 | 16.9 |
| 250 | 2 | 0.24 | 0.48 | 2.01 | 7.63 | 10.4 | 13.7 | 17.3 | 16.1 | 49.8 |
| 500 | 2 | 0.24 | 0.24 | 1.12 | 6.02 | 6.83 | 7.63 | 11.6 | 11.2 | 36.9 |
| 750 | 2 | 0.24 | 0.24 | 2.01 | 4.42 | 5.22 | 6.02 | 8.03 | 10 | 27.9 |
| 1000 | 2 | 0 | 0.24 | 1.2 | 2.81 | 3.61 | 4.82 | 6.83 | 10 | 24.3 |
| 250 | 3 | 0 | 0 | 0 | 0 | 0 | 0 | 0 | 0 | 4.82 |
| 500 | 3 | 0 | 0 | 0 | 0 | 0 | 0 | 0 | 0 | 2.41 |
| 750 | 3 | 0 | 0 | 0 | 0 | 0 | 0 | 0 | 0 | 0 |
| 1000 | 3 | 0 | 0 | 0 | 0 | 0 | 0 | 0 | 0 | 0 |
| 250 | 4 | 0 | 0 | 0 | 0 | 0 | 0 | 0 | 0 | 0 |
| 500 | 4 | 0 | 0 | 0 | 0 | 0 | 0 | 0 | 0 | 0 |
| 750 | 4 | 0 | 0 | 0 | 0 | 0 | 0 | 0 | 0 | 0 |
| 1000 | 4 | 0 | 0 | 0 | 0 | 0 | 0 | 0 | 0 | 0 |
| 250 | 5 | 4.82 | 5.62 | 5.62 | 6.43 | 7.23 | 8.03 | 10 | 10 | 13.3 |
| 500 | 5 | 0.8 | 0.8 | 1.2 | 2.41 | 2.81 | 2.81 | 2.41 | 4.82 | 6.83 |
| 750 | 5 | 0.8 | 0.8 | 2.01 | 2.01 | 2.81 | 3.61 | 4.42 | 4.42 | 4.82 |
| 1000 | 5 | 0 | 0 | 0.8 | 0.8 | 1.2 | 1.2 | 1.2 | 1.2 | 2.81 |
| 250 | 6 | 1.2 | 1.2 | 3.61 | 6.83 | 9.24 | 10.4 | 11.2 | 15.3 | 36.9 |
| 500 | 6 | 0 | 1.2 | 1.2 | 1.2 | 2.41 | 4.02 | 4.82 | 8.84 | 18.7 |
| 750 | 6 | 0 | 0 | 0 | 0 | 0 | 0.8 | 0.8 | 0.8 | 4.82 |
| 1000 | 6 | 0 | 0 | 0 | 0 | 0 | 0.4 | 0.4 | 1.2 | 1.2 |
| 250 | 7 | 0 | 0 | 1.2 | 1.2 | 1.2 | 1.2 | 1.2 | 1.2 | 1.2 |
| 500 | 7 | 0 | 0 | 0.8 | 1.2 | 1.2 | 1.2 | 6.02 | 7.23 | 8.84 |
| 750 | 7 | 0 | 0 | 1.61 | 2.41 | 2.01 | 3.21 | 3.21 | 5.22 | 12.9 |
| 1000 | 7 | 0 | 0 | 0 | 0 | 0.4 | 1.61 | 3.21 | 6.43 | 25.7 |
| 1250 | 7 | 0 | 0 | 0 | 0 | 4.82 | 9.64 | 14.5 | 19.3 | 38.6 |
| 1500 | 7 | 0 | 0 | 0 | 0 | 1.2 | 4.82 | 9.64 | 16.9 | 27.7 |
| 2000 | 7 | 0 | 0 | 0 | 0 | 1.2 | 2.41 | 4.82 | 9.64 | 12 |
| 2250 | 7 | 0 | 0 | 0 | 0 | 0 | 0 | 1.2 | 2.41 | 4.82 |
| 2500 | 7 | 0 | 0 | 0 | 0 | 0 | 0 | 0 | 0 | 0 |

Test plates that had 2500 ppm of DDAC in the agar solutions did not show growth of tested microorganisms.

TABLE 5

The growth of *Aspergillus niger* (1), *Gliocladium roseum* (2), *Aureobasidium pullulans* (3), *Ceratocistis adiposa* (4), *Chatemonium globosum* (5), *Coriolus Versicolor* (6), and *Coniphora puteana* (7) in the agar media containing selected concentrations of ITA.

| Concentration (ppm) | Fungi ( ) | Incubation Period (days) | | | | | | | | |
|---|---|---|---|---|---|---|---|---|---|---|
| | | 1 | 2 | 3 | 4 | 5 | 6 | 7 | 11 | 22 |
| | | | | | Growth Rate (%) | | | | | |
| 10 | 1 | 0 | 1.2 | 3.01 | 7.23 | 9.64 | 9.64 | 16.9 | 43.4 | 86.7 |
| 15 | 1 | 0 | 0 | 0 | 0 | 0 | 0 | 0 | 0 | 0 |
| 25 | 1 | 0 | 0 | 0 | 0 | 0 | 0 | 0 | 0 | 0 |
| 50 | 1 | 0 | 0 | 0 | 0 | 0 | 0 | 0 | 0 | 0 |
| 10 | 2 | 0 | 0 | 4.22 | 13.3 | 18.1 | 24.1 | 28.9 | 69.9 | 100 |
| 15 | 2 | 0 | 0 | 4.82 | 9.64 | 12 | 16.9 | 24.1 | 48.2 | 62.7 |
| 25 | 2 | 0 | 0 | 0.8 | 1.61 | 3.21 | 4.02 | 6.43 | 12.9 | 20.9 |
| 50 | 2 | 0 | 0 | 0 | 0 | 0 | 0 | 0 | 0 | 0 |
| 10 | 3 | 0 | 0 | 0 | 0 | 0 | 0 | 0 | 7.23 | 22.5 |
| 15 | 3 | 0 | 0 | 0 | 0 | 0 | 0 | 0 | 0 | 0 |
| 25 | 3 | 0 | 0 | 0 | 0 | 0 | 0 | 0 | 0 | 0 |
| 50 | 3 | 0 | 0 | 0 | 0 | 0 | 0 | 0 | 0 | 0 |
| 10 | 4 | 0 | 0 | 0 | 0 | 0 | 0 | 0 | 0 | 0 |
| 15 | 4 | 0 | 0 | 0 | 0 | 0 | 0 | 0 | 0 | 0 |
| 25 | 4 | 0 | 0 | 0 | 0 | 0 | 0 | 0 | 0 | 0 |
| 50 | 4 | 0 | 0 | 0 | 0 | 0 | 0 | 0 | 0 | 0 |

TABLE 5-continued

The growth of Aspergillus niger (1), Gliocladium roseum (2), Aureobasidium pullulans (3), Ceratocistis adiposa (4), Chatemonium globosum (5), Coriolus Versicolor (6), and Coniphora puteana (7) in the agar media containing selected concentrations of ITA.

| Concentration (ppm) | Fungi ( ) | Incubation Period (days) | | | | | | | | |
|---|---|---|---|---|---|---|---|---|---|---|
| | | 1 | 2 | 3 | 4 | 5 | 6 | 7 | 11 | 22 |
| | | | | | Growth Rate (%) | | | | | |
| 10 | 5 | 0 | 0.6 | 1.2 | 2.41 | 2.41 | 3.01 | 3.01 | 8.43 | 13.3 |
| 15 | 5 | 0 | 0 | 0 | 0 | 0 | 0 | 0 | 0 | 0 |
| 25 | 5 | 0 | 0 | 0 | 0 | 0 | 0 | 0 | 0 | 0 |
| 50 | 5 | 0 | 0 | 0 | 0 | 0 | 0 | 0 | 0 | 0 |
| 10 | 6 | 0 | 0 | 0 | 0 | 0 | 0 | 8.03 | 17.7 | 100 |
| 15 | 6 | 0 | 0 | 0 | 0 | 0 | 0 | 1.61 | 8.03 | 33.3 |
| 25 | 6 | 0 | 0 | 0 | 0 | 0 | 0 | 0 | 0 | 0 |
| 50 | 6 | 0 | 0 | 0 | 0 | 0 | 0 | 0 | 0 | 0 |
| 10 | 7 | 0 | 0 | 0 | 0 | 0 | 0 | 0 | 0 | 0 |
| 15 | 7 | 0 | 0 | 0 | 0 | 0 | 0 | 0 | 0 | 0 |
| 25 | 7 | 0 | 0 | 0 | 0 | 0 | 0 | 0 | 0 | 0 |
| 50 | 7 | 0 | 0 | 0 | 0 | 0 | 0 | 0 | 0 | 0 |

DDAC and ITA are combined in mixtures to extend the spectrum of antifungal activity and counteract the development of fungicide resistance.

Generally, the expected response of a mixture of two chemicals is the sum of the effects if the components separately. On the other hand, additional advantages of the mixture could be obtained due to synergistic interactions by which the efficiency of the individual components is increased and at the same time the amount of active ingredients is reduced. In this case, the effectiveness of the mixture can not be computed from that of the individual ingredients.

Synergism is defined as the simultaneous action of two or more compounds in which total response of an organism to the fungicide combination is greater than the sum of the individual components.

In order to show more graphically the possible synergy in the invention, the results are presented by applying the Synergy Index (S.I.). This method shares similarities with the Synergy Index, that is reported in U.S. Pat. Nos. 4,906,651 and 5,131,939, but it is modified for this particular bioassay. In long-term effects of a potential preservative, the $22^{nd}$ day of the experiment was chosen to define a reference point (RP). Minimum biocidal concentration of the potential wood preservatives (mixture of DDAC and ITA) are analyzed using the following equation:

$$(MCA'/MCA)+(MCB'/MCB)=SI \text{ or } SI_A+SI_B=SI$$

wherein: $(MCA'/MCA)=SI_A$ and $(MCB'/MCB)=SI_B$

MCA=Concentration of compound A in parts per million, acting alone, which prevents fungal growth at the reference point MCA'=Concentration of compound A in parts per million, in the mixture, which prevents fungal growth at the reference point MCB=Concentration of compound B in parts per million, acting alone, which prevents fungal growth at the reference point MCB'=Concentration of compound B in parts per million, in the mixture, which prevents fungal growth at the reference point When the sum of ratios $(MCA'/MCA)=SI_A$ and $(MCB'/MCB)=SI_B$ is greater than one, antagonism is indicated. When the sum of $SI_A$ and $SI_B$ is equal to one, compatibility is demonstrated. When the sum of $SI_A$ and $SI_B$ is less than one, synergy is demonstrated. The smaller the sum, the higher the synergistic effect.

Synergy Index is represented by the formula:

$$S.I.=\text{Log}(SI)$$

Table 6 (6-1, 6-2, 6-3, 6-4, 6-5, 6-6, and 6-7) represents an anti-fungal activity of wood preservatives that is a combination of selected concentrations of DDAC and ITA. The simultaneous activity of two substances can be expressed as Synergy Index, which is positive in the case of antagonism, and negative in the event of synergism.

TABLE 6-1

Synergistic Anti-Aspergilus niger activity of the combination of DDAC (A) and ITA (B)

| Quantity producing end points | | | Mixture % | | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 25 | 4 | 125 | 80 | 20 | 0.04 | 0.5 | 0.54 | −0.27 |
| 250 | 25 | 10 | 275 | 90.9 | 9.09 | 0.1 | 0.5 | 0.6 | −0.22 |
| 500 | 15 | 33.333 | 515 | 97.1 | 2.91 | 0.2 | 0.3 | 0.5 | −0.3 |
| 500 | 25 | 20 | 525 | 95.2 | 4.76 | 0.2 | 0.5 | 0.7 | −0.15 |
| 750 | 10 | 75 | 760 | 98.7 | 1.32 | 0.3 | 0.2 | 0.5 | −0.3 |
| 750 | 15 | 50 | 765 | 98 | 1.96 | 0.3 | 0.3 | 0.6 | −0.22 |

TABLE 6-1-continued

Synergistic Anti-*Aspergilus niger* activity of the combination of DDAC (A) and ITA (B)

| Quantity producing end points | | | Mixture % | | | Ratios | | | Activity |
|---|---|---|---|---|---|---|---|---|---|
| QA | QB | Ratio | Total | A | B | QA/Qa | QB/Qb | SUM | Index |
| 750 | 25 | 30 | 775 | 96.8 | 3.23 | 0.3 | 0.5 | 0.8 | −0.1 |
| 1000 | 10 | 100 | 1010 | 99 | 0.99 | 0.4 | 0.2 | 0.6 | −0.22 |
| 1000 | 15 | 66.667 | 1015 | 98.5 | 1.48 | 0.4 | 0.3 | 0.7 | −0.15 |
| 1000 | 25 | 40 | 1025 | 97.6 | 2.44 | 0.4 | 0.5 | 0.9 | −0.05 |
| 2500 | 0 | 0 | 2500 | 100 | 0 | 1 | 0 | 1 | 0 |

TABLE 6-2

Synergistic Anti-*Gliocladium roseum* activity of the various combination of DDAC (A) and ITA (B)

| Quantity producing end points | | | Mixture % | | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 25 | 4 | 125 | 80 | 20 | 0.04 | 0.5 | 0.54 | −0.27 |
| 250 | 15 | 16.667 | 265 | 94.3 | 5.66 | 0.1 | 0.3 | 0.4 | −0.4 |
| 250 | 25 | 10 | 275 | 90.9 | 9.09 | 0.1 | 0.5 | 0.6 | −0.22 |
| 500 | 25 | 20 | 525 | 95.2 | 4.76 | 0.2 | 0.5 | 0.7 | −0.15 |
| 750 | 15 | 50 | 765 | 98 | 1.96 | 0.3 | 0.3 | 0.6 | −0.22 |
| 750 | 25 | 30 | 775 | 96.8 | 3.23 | 0.3 | 0.5 | 0.8 | −0.1 |
| 1000 | 25 | 40 | 1025 | 97.6 | 2.44 | 0.4 | 0.5 | 0.9 | −0.05 |
| 2500 | 0 | 0 | 2500 | 100 | 0 | 1 | 0 | 1 | 0 |

TABLE 6-3

Synergistic Anti-*Auroebasidium pullulans* activity of the various combination of DDAC (A) and ITA (B)

| Quantity producing end points | | | Mixture % | | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 15 | 6.6667 | 115 | 87 | 13 | 0.04 | 0.3 | 0.34 | −0.47 |
| 100 | 25 | 4 | 125 | 80 | 20 | 0.04 | 0.5 | 0.54 | −0.27 |
| 250 | 15 | 16.667 | 265 | 94.3 | 5.66 | 0.1 | 0.3 | 0.4 | −0.4 |
| 250 | 25 | 10 | 275 | 90.9 | 9.09 | 0.1 | 0.5 | 0.6 | −0.22 |
| 500 | 10 | 50 | 510 | 98 | 1.96 | 0.2 | 0.2 | 0.4 | −0.4 |
| 500 | 15 | 33.333 | 515 | 97.1 | 2.91 | 0.2 | 0.3 | 0.5 | −0.3 |
| 500 | 25 | 20 | 525 | 95.2 | 4.76 | 0.2 | 0.5 | 0.7 | −0.15 |
| 750 | 10 | 75 | 760 | 98.7 | 1.32 | 0.3 | 0.2 | 0.5 | −0.3 |
| 750 | 15 | 50 | 765 | 98 | 1.96 | 0.3 | 0.3 | 0.6 | −0.22 |
| 750 | 25 | 30 | 775 | 96.8 | 3.23 | 0.3 | 0.5 | 0.8 | −0.1 |
| 1000 | 10 | 100 | 1010 | 99 | 0.99 | 0.4 | 0.2 | 0.6 | −0.22 |
| 1000 | 15 | 66.667 | 1015 | 98.5 | 1.48 | 0.4 | 0.3 | 0.7 | −0.15 |
| 1000 | 25 | 40 | 1025 | 97.6 | 2.44 | 0.4 | 0.5 | 0.9 | −0.05 |
| 2500 | 0 | 0 | 2500 | 100 | 0 | i | 0 | 1 | 0 |

TABLE 6-4

Synergistic Anti-*Ceratocistis adiposa* activity of the various combinations of DDAC (A) and ITA (B)

| Quantity producing end points | | | | Mixture % | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 15 | 6.6667 | 115 | 87 | 13 | 0.04 | 0.3 | 0.34 | −0.47 |
| 100 | 25 | 4 | 125 | 80 | 20 | 0.04 | 0.5 | 0.54 | −0.27 |
| 250 | 25 | 10 | 275 | 90.9 | 9.09 | 0.1 | 0.5 | 0.6 | −0.22 |
| 500 | 10 | 50 | 510 | 98 | 1.96 | 0.2 | 0.2 | 0.4 | −0.4 |
| 500 | 15 | 33.333 | 515 | 97.1 | 2.91 | 0.2 | 0.3 | 0.5 | −0.3 |
| 500 | 25 | 20 | 525 | 95.2 | 4.76 | 0.2 | 0.5 | 0.7 | −0.15 |
| 750 | 10 | 75 | 760 | 98.7 | 1.32 | 0.3 | 0.2 | 0.5 | −0.3 |
| 750 | 15 | 50 | 765 | 98 | 1.96 | 0.3 | 0.3 | 0.6 | −0.22 |
| 750 | 25 | 30 | 775 | 96.8 | 3.23 | 0.3 | 0.5 | 0.8 | −0.1 |
| 1000 | 10 | 100 | 1010 | 99 | 0.99 | 0.4 | 0.2 | 0.6 | −0.22 |
| 1000 | 15 | 66.667 | 1015 | 98.5 | 1.48 | 0.4 | 0.3 | 0.7 | −0.15 |
| 1000 | 25 | 40 | 1025 | 97.6 | 2.44 | 0.4 | 0.5 | 0.9 | −0.05 |
| 2500 | 0 | 0 | 2500 | 100 | 0 | 1 | 0 | 1 | 0 |

TABLE 6-5

Synergistic Anti-*Chatemonium globosum* activity of the various combinations of DDAC (A) and ITA (B)

| Quantity producing end points | | | | Mixture % | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 25 | 4 | 125 | 80 | 20 | 0.04 | 0.5 | 0.54 | −0.27 |
| 250 | 25 | 10 | 275 | 90.9 | 9.09 | 0.1 | 0.5 | 0.6 | −0.22 |
| 500 | 15 | 33.333 | 515 | 97.1 | 2.91 | 0.2 | 0.3 | 0.5 | −0.3 |
| 500 | 25 | 20 | 525 | 95.2 | 4.76 | 0.2 | 0.5 | 0.7 | −0.15 |
| 750 | 10 | 75 | 760 | 98.7 | 1.32 | 0.3 | 0.2 | 0.5 | −0.3 |
| 750 | 15 | 50 | 765 | 98 | 1.96 | 0.3 | 0.3 | 0.6 | −0.22 |
| 750 | 25 | 30 | 775 | 96.8 | 3.23 | 0.3 | 0.5 | 0.8 | −0.1 |
| 1000 | 15 | 66.667 | 1015 | 98.5 | 1.48 | 0.4 | 0.3 | 0.7 | −0.15 |
| 1000 | 25 | 40 | 1025 | 97.6 | 2.44 | 0.4 | 0.5 | 0.9 | −0.05 |
| 2500 | 0 | 0 | 2500 | 100 | 0 | 1 | 0 | 1 | 0 |

TABLE 6-6

Synergistic Anti-*Coriulus versicolor* activity of the various combinations of DDAC (A) and ITA (B)

| Quantity producing end points | | | | Mixture % | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 15 | 6.6667 | 115 | 87 | 13 | 0.04 | 0.3 | 0.34 | −0.47 |
| 100 | 25 | 4 | 125 | 80 | 20 | 0.04 | 0.5 | 0.54 | −0.27 |
| 250 | 15 | 16.667 | 265 | 94.3 | 5.66 | 0.1 | 0.3 | 0.4 | −0.4 |
| 250 | 25 | 10 | 275 | 90.9 | 9.09 | 0.1 | 0.5 | 0.6 | −0.22 |
| 500 | 10 | 50 | 510 | 98 | 1.96 | 0.2 | 0.2 | 0.4 | −0.4 |
| 500 | 15 | 33.333 | 515 | 97.1 | 2.91 | 0.2 | 0.3 | 0.5 | −0.3 |
| 500 | 25 | 20 | 525 | 95.2 | 4.76 | 0.2 | 0.5 | 0.7 | −0.15 |
| 750 | 10 | 75 | 760 | 98.7 | 1.32 | 0.3 | 0.2 | 0.5 | −0.3 |
| 750 | 15 | 50 | 765 | 98 | 1.96 | 0.3 | 0.3 | 0.6 | −0.22 |
| 750 | 25 | 30 | 775 | 96.8 | 3.23 | 0.3 | 0.5 | 0.8 | −0.1 |
| 1000 | 10 | 100 | 1010 | 99 | 0.99 | 0.4 | 0.2 | 0.6 | −0.22 |
| 1000 | 15 | 66.667 | 1015 | 98.5 | 1.48 | 0.4 | 0.3 | 0.7 | −0.15 |
| 1000 | 25 | 40 | 1025 | 97.6 | 2.44 | 0.4 | 0.5 | 0.9 | −0.05 |
| 2500 | 0 | 0 | 2500 | 100 | 0 | 1 | 0 | 1 | 0 |

TABLE 6-7

Synergistic Anti-*Coniphora puteana* activity of the various combinations of DDAC (A) and ITA (B)

| Quantity producing end points | | | | Mixture % | | Ratios | | | Activity |
|---|---|---|---|---|---|---|---|---|---|
| QA | QB | Ratio | Total | A | B | QA/Qa | QB/Qb | SUM | Index |
| 0 | 50 | | 50 | 0 | 100 | 0 | 1 | 1 | 0 |
| 100 | 15 | 100/15 | 115 | 87 | 13 | 0.04 | 0.3 | 0.34 | −0.47 |
| 100 | 25 | 100/25 | 125 | 80 | 20 | 0.04 | 0.5 | 0.54 | −0.27 |
| 250 | 15 | 250/25 | 265 | 94.3 | 5.66 | 0.1 | 0.3 | 0.4 | −0.4 |
| 250 | 25 | 250/25 | 275 | 90.9 | 9.09 | 0.1 | 0.5 | 0.6 | −0.22 |
| 500 | 10 | 500/10 | 510 | 98 | 1.96 | 0.2 | 0.2 | 0.4 | −0.4 |
| 500 | 15 | 500/15 | 515 | 97.1 | 2.91 | 0.2 | 0.3 | 0.5 | −0.3 |
| 500 | 25 | 500/25 | 525 | 95.2 | 4.76 | 0.2 | 0.5 | 0.7 | −0.15 |
| 750 | 10 | 750/10 | 760 | 98.7 | 1.32 | 0.3 | 0.2 | 0.5 | −0.3 |
| 750 | 15 | 750/15 | 765 | 98 | 1.96 | 0.3 | 0.3 | 0.6 | −0.22 |
| 750 | 25 | 750/25 | 775 | 96.8 | 3.23 | 0.3 | 0.5 | 0.8 | −0.1 |
| 1000 | 10 | 1000/10 | 1010 | 99 | 0.99 | 0.4 | 0.2 | 0.6 | −0.22 |
| 1000 | 15 | 1000/15 | 1015 | 98.5 | 1.48 | 0.4 | 0.3 | 0.7 | −0.15 |
| 1000 | 25 | 1000/25 | 1025 | 97.6 | 2.44 | 0.4 | 0.5 | 0.9 | −0.05 |
| 2500 | 0 | 0 | 2500 | 100 | 0 | 1 | 0 | 1 | 0 |

The data presented in Table 6 (6-1, 6-2, 6-3, 6-4, 6-5, and 6-7) represent examples of combinations of DDAC and ITA that anticipated a synergistic effect. They indicate that relatively low concentrations of ITA enhance the fIngicidal activity of DDAC and that this enhancement extends over a wide range of concentrations.

EXAMPLE 2

According to the results presented at Table 4, unlike all other microorganisms, *Coniphora puteana* showed an increasing growth rate as a concentration of DDAC increased. These indicate the possibility that *Conifora puteana* may develop resistance to DDAC (if the concentration is not sufficient) and potentially use it as food.

Results from Table 4 (microorganism: #7) which represent *Coniphora puteana*'s growth rate, are showed in Chart 2.

In order to counteract these phenomena and to have a broadened activity spectrum of preservative, the selected amount of ITA was mixed with DDAC. The results which represent the growth of *Coniphora puteana* on the agar media containing combinations of selected concentrations of DDAC and ITA are represented in Table 7.

TABLE 7

The Growth Rate of *Coniphora puteana* on the Media Containing Selected Combinations of DDAC and ITA

| Mixture Concentration | | Incubation Period (days) | | | | | | | | |
|---|---|---|---|---|---|---|---|---|---|---|
| DDAC (ppm) | ITA (ppm) | 1 | 2 | 3 | 4 | 5 | 6 | 7 | 11 | 22 |
| | | Growth Rate (%) | | | | | | | | |
| 2500 | 150 | 0 | 0 | 0 | 0 | 0 | 0 | 0 | 0 | 0 |
| 750 | 10 | 0 | 0 | 0 | 0 | 0 | 0 | 0 | 0 | 0 |
| 750 | 15 | 0 | 0 | 0 | 0 | 0 | 0 | 0 | 0 | 0 |
| 750 | 25 | 0 | 0 | 0 | 0 | 0 | 0 | 0 | 0 | 0 |
| 500 | 10 | 0 | 0 | 0 | 0 | 0 | 0 | 0 | 0 | 0 |
| 500 | 15 | 0 | 0 | 0 | 0 | 0 | 0 | 0 | 0 | 0 |
| 500 | 25 | 0 | 0 | 0 | 0 | 0 | 0 | 0 | 0 | 0 |
| 1000 | 10 | 0 | 0 | 0 | 0 | 0 | 0 | 0 | 0 | 0 |
| 1000 | 15 | 0 | 0 | 0 | 0 | 0 | 0 | 0 | 0 | 0 |
| 1000 | 25 | 0 | 0 | 0 | 0 | 0 | 0 | 0 | 0 | 0 |
| 250 | 10 | 0 | 0 | 0.8 | 1.61 | 2.41 | 2.41 | 3.21 | 6.43 | 16.1 |
| 250 | 15 | 0 | 0 | 0 | 0 | 0 | 0 | 0 | 0 | 0 |
| 250 | 25 | 0 | 0 | 0 | 0 | 0 | 0 | 0 | 0 | 0 |
| 100 | 25 | 0 | 0 | 0 | 0 | 0 | 0 | 0 | 0 | 0 |
| 1000 | 5 | 0 | 0 | 0 | 2.41 | 4.02 | 4.82 | 9.24 | 18.1 | 39 |
| 100 | 15 | 0 | 0 | 0 | 0 | 0 | 0 | 0 | 0 | 0 |
| 750 | 7.5 | 0 | 0 | 0 | 0.4 | 0.8 | 3.21 | 6.02 | 10.4 | 22.5 |
| 1000 | 7.5 | 0 | 0 | 0 | 0 | 0.4 | 2.41 | 3.21 | 7.23 | 17.7 |
| 500 | 7.5 | 0 | 0 | 0 | 0 | 2.41 | 4.02 | 4.82 | 6.43 | 27.1 |

The results from Table 7 prove that the present invention, a synergistic wood preservative composition comprising of ITA and DDAC, provides enhanced protection against the organisms that may develop resistance to DDAC (e.g. Coniphora), and therefore broaden the spectrum of activities.

What is claimed:

1. A synergistic wood preservative composition consisting of a mixture of a first component, a second component, and a solvent, wherein the first component is a mixture of 5-chloro-2-methyl-4-isothiazolin-3-one and 2-methyl-4-isothiazolin-3-one;

and the second component is a quaternary ammonium compound selected from the group consisting of consisting of didecyldimethylammonium chloride, trimethyl-coco-ammonium chloride, dimethyl-di-coco-ammonium chloride, and mixtures thereof.

2. The synergistic wood preservative of claim 1, wherein the first component is a 3:1 mixture by weight of 5-chloro-2-methyl-4-isothiazolin-3-one and 2-methyl-4-isothiazolin-3-one.

3. The composition of claim 1 wherein the ratio of the first component to the second component ranges from about 5:1 to about 1:300 parts by weight.

4. The composition of claim 1 wherein the ratio of the first component to the second component ranges from about 1:2 to about 1:100 parts by weight.

5. The composition of claim 1 wherein the ratio of the first component to the second component ranges from about 1:30 to about 1:200 parts by weight.

6. The composition of claim 1 wherein the ratio of the first component to the second component ranges from about 1:40 to about 1:130 parts by weight.

7. The composition of claim 1 which provides protection against DDAC tolerant microorganisms.

8. The composition of claim 1 which provides protection of wood against mould, stain, and wood destroying microorganisms.

9. Process for preserving wood by applying the synergistic wood preservative composition of claim 1 in which the composition is applied by spraying the wood.

10. Process for preserving wood by applying a synergistic wood preservative of claim 1 by dipping the wood in the composition.

11. The composition of claim 1, wherein said ammonium compound is didecyldimethyl ammonium chloride.

12. The composition of claim 1, wherein said ammonium compound is tri-methyl-coco-ammonium chloride.

13. The composition of claim 1, wherein said ammonium compound is dimethyl-di-coco-ammonium chloride.

* * * * *